US009348972B2

(12) United States Patent
Yao

(10) Patent No.: US 9,348,972 B2
(45) Date of Patent: May 24, 2016

(54) METHOD OF ASSESSING RISK OF MULTIPLE BIRTHS IN INFERTILITY TREATMENTS

(75) Inventor: Mylene Yao, Los Altos, CA (US)

(73) Assignee: UNIVFY Inc., Los Altos, CA (US)

( * ) Notice: Subject to any disclaimer, the term of this patent is extended or adjusted under 35 U.S.C. 154(b) by 383 days.

(21) Appl. No.: 13/182,360

(22) Filed: Jul. 13, 2011

(65) Prior Publication Data

US 2012/0016184 A1    Jan. 19, 2012

Related U.S. Application Data

(60) Provisional application No. 61/363,650, filed on Jul. 13, 2010.

(51) Int. Cl.
*A61B 17/425* (2006.01)
*A61B 17/435* (2006.01)
*A61D 19/04* (2006.01)
*G06F 19/00* (2011.01)

(52) U.S. Cl.
CPC ........... *G06F 19/3431* (2013.01); *A61B 17/425* (2013.01); *A61B 17/435* (2013.01); *A61D 19/04* (2013.01)

(58) Field of Classification Search
CPC ..... A61B 17/425; A61B 17/435; A61D 19/04
USPC .......................................................... 600/33
See application file for complete search history.

(56) References Cited

U.S. PATENT DOCUMENTS

| | | | |
|---|---|---|---|
| 4,816,257 A * | 3/1989 | Buster et al. .................. | 424/430 |
| 5,612,869 A | 3/1997 | Letzt et al. | |
| 5,619,991 A | 4/1997 | Sloane | |
| 5,809,997 A | 9/1998 | Wolf | |
| 5,812,984 A | 9/1998 | Goltra | |
| 5,816,246 A | 10/1998 | Mirza | |
| 5,832,450 A | 11/1998 | Myers et al. | |
| 5,924,074 A | 7/1999 | Evans | |
| 6,347,329 B1 | 2/2002 | Evans | |
| 6,523,009 B1 | 2/2003 | Wilkins | |
| 6,529,876 B1 | 3/2003 | Dart et al. | |
| 6,597,946 B2 | 7/2003 | Avrahami et al. | |
| 6,600,696 B1 | 7/2003 | Lynn | |
| 7,076,437 B1 | 7/2006 | Levy | |
| 7,188,073 B1 | 3/2007 | Tam et al. | |
| 7,188,082 B2 | 3/2007 | Keane et al. | |
| 7,263,493 B1 | 8/2007 | Provost | |
| 7,275,220 B2 | 9/2007 | Brummel et al. | |
| 7,295,988 B1 | 11/2007 | Reeves | |
| 7,311,666 B2 | 12/2007 | Stupp et al. | |
| 7,361,142 B2 | 4/2008 | Suda | |
| 7,392,199 B2 | 6/2008 | Karlov et al. | |
| 7,438,228 B2 | 10/2008 | Robertson et al. | |
| 7,461,079 B2 | 12/2008 | Walker et al. | |
| 7,487,102 B2 | 2/2009 | Castille | |
| 7,643,969 B2 | 1/2010 | Soto et al. | |
| 7,685,000 B1 | 3/2010 | Petit | |
| 7,703,042 B2 | 4/2010 | Brummel et al. | |
| 7,730,024 B2 | 6/2010 | Harinath | |
| 7,853,456 B2 | 12/2010 | Soto et al. | |
| 8,160,977 B2 | 4/2012 | Poulin | |
| 2003/0017481 A1 | 1/2003 | Golub et al. | |
| 2005/0202426 A1* | 9/2005 | Short et al. ................... | 435/6 |
| 2006/0052945 A1 | 3/2006 | Rabinowitz et al. | |
| 2006/0173663 A1 | 8/2006 | Langheier et al. | |
| 2007/0027636 A1 | 2/2007 | Rabinowitz et al. | |
| 2007/0053563 A1 | 3/2007 | Tu et al. | |
| 2007/0055552 A1 | 3/2007 | St. Clair et al. | |
| 2007/0082329 A1 | 4/2007 | Williams et al. | |
| 2007/0130206 A1 | 6/2007 | Zhou et al. | |
| 2007/0162992 A1* | 7/2007 | Burns .............................. | 800/21 |
| 2007/0178501 A1 | 8/2007 | Rabinowitz et al. | |
| 2007/0192134 A1 | 8/2007 | Littenberg et al. | |
| 2007/0238111 A1 | 10/2007 | Cibelli et al. | |
| 2008/0133275 A1 | 6/2008 | Haug et al. | |
| 2008/0162992 A1 | 7/2008 | Lonowski | |
| 2008/0163824 A1* | 7/2008 | Moser et al. ................... | 119/174 |
| 2009/0029375 A1 | 1/2009 | Jupe et al. | |
| 2009/0259491 A1 | 10/2009 | Busch | |
| 2010/0036192 A1* | 2/2010 | Yao et al. ....................... | 600/33 |
| 2010/0049689 A1 | 2/2010 | Jorg et al. | |
| 2010/0112605 A1 | 5/2010 | Paul et al. | |
| 2010/0138199 A1 | 6/2010 | Soto et al. | |
| 2010/0191040 A1* | 7/2010 | Hsueh et al. ..................... | 600/33 |
| 2011/0173018 A1 | 7/2011 | Hoffner et al. | |
| 2011/0288780 A1 | 11/2011 | Rabinowitz et al. | |
| 2011/0313790 A1 | 12/2011 | Yao | |

FOREIGN PATENT DOCUMENTS

WO    2010045463 A2    4/2010

OTHER PUBLICATIONS

Urbancsek et al., "Serum human chorionic gonadotropin measurements may predict pregnancy outcome and multiple gestation after in vitro fertilization," Fertility and Sterility, vol. 78, No. 3, Sep. 2002.*
Bortolus et al., "The epidemiology of multiple births," Human Reproductive Update 1999, vol. 5, No. 2, pp. 179-187.*
Hunault et al., "A prediction model for selecting patient undergoing in vitro fertilization for elective single embryo transfer," Fertility and Sterility, vol. 77, No. 4, Apr. 2002.*
Stern et al., "Optimizing the number of cleavage stage embryos to transfer on day 3 in women 38 years of age and older: a Society for Assisted Reproductive Technology database study," Fertility and Sterility, vol. 91, No. 3, Mar. 2009, p. 767-776.*
Valbuena et al., "Factors responsible for multiple pregnancies after ovarian stimulation and intrauterine insemination with gonadotropins," Journal of Assisted Reproduction and Genetics, vol. 13, No. 8, 1996, p. 663-668.*

(Continued)

*Primary Examiner* — Charles A Marmor, II
*Assistant Examiner* — Thaddeus Cox
(74) *Attorney, Agent, or Firm* — Karen Canaan; CanaanLaw, P.C.

(57) ABSTRACT

Provided is a multiple birth prognostic tool that is used to analyze data in order to predict a multiple birth event in a female human patient undergoing an infertility treatment. The MBP prognostic tool may also be used to enhance the accuracy of diagnostic or prognostic tests that predict embryo viability. The MBP prognostic tool of the present invention may be clinic specific or it may be modified to be used in a multi-clinic approach.

25 Claims, No Drawings

(56) References Cited

OTHER PUBLICATIONS

International Search Report dated Nov. 17, 2011, for counterpart application No. PCT/US11/43921, (inventor Mylene Yao; filed on Jul. 13, 2011).
American Society for Reproductive Medicine (ASRM), Guidelines on Number of Embryos Transferred, Fertility and Sterility 90:S163-S164 (2008).
Banerjee et al., Deep Phenotyping to Predict Live Birth Outcomes in In Vitro Fertilization, PNAS 107 (31):13570-13575 (2010).
Bonduelle et al., A Multi-Centre Cohort Study of the Physical Health of 5-Year-Old Children Conceived After Intracytoplasmic Sperm Injection, In Vitro Fertilization and Natural Conception, Human Reproduction 20(2):413-419 (2005).
Friedman, Greedy Function Approximation: A Gradient Boosting Machine, IMS 1999 Reitz Lecture, Feb. 24, 1999 (modified Mar. 15, 2000 and Apr. 15, 2001).
Friedman, Stochastic Gradient Boosting, Stanford University Technical Paper, Mar. 26, 1999.
Friedman, Tutorial: Getting Started in MART with R, Stanford University Technical Paper, May 13, 2002.
Friedman et al., Multiple Additive Regression Trees with Application in Epidemiology, Statistics in Medicine 22:1365-1381 (2003).
Kalu et al., Reducing Multiple Pregnancy in Assisted Reproduction Technology: Towards a Policy of Single Blastocyst Transfer in Younger Women, British Journal of Obstetrics and Gynecology (BJOG) 115:1143-1150 (2008).
Khalaf et al., Selective Single Blastocyst Transfer Reduces the Multiple Pregnancy Rate and Increases Pregnancy Rates: A Pre- and Postintervention Study, British Journal of Obstetrics and Gynecology (BJOG) 115:385-390 (2008).
Martin et al., Births: Final Data for 2006, National Vital Statistics Reports (NVSR) 57(7):1-102 (2009).
Osterman et al., Expanded Health Data From the New Birth Certificate, 2006, National Vital Statistics Reports (NVSR) 58(5):1-24 (2009).
Pinborg et al., Neonatal Outcome in a Danish National Cohort of 8602 Children Born After In Vitro Fertilization or Intracytoplasmic Sperm Injection: The Role of Twin Pregnancy, Acta Obstet Gynecol Scand 83: 1071-1078 (2004).
Styer et al., Single-Blastocyst Transfer Decreases Twin Gestation Without Affecting Pregnancy Outcome, Fertility and Sterility 89(6):1702-1708 (2008).
Sunderam et al., Assisted Reproductive Technology Surveillance—United States, 2006, Morbidity and Mortality Weekly Report (MMWR) 58(SS05):1-25 (2009).
Sutcliffe et al., Outcome of Assisted Reproduction (Review), Lancet 370:351-59 (2007).
Van Voorhis, In Vitro Fertilization, The New England Journal of Medicine 356:379-86 (2007).
Horvitz, From Data to Predictions and Decisions: Enabling Evidence-Based Healthcare, Computing Community Consortium, Version 6: Sep. 16, 2010.
Hseih et al., Decreased Expression of Mitochondrial Genes in Human Unfertilized Oocytes and Arrested Embryos, Fertility and Sterility 81 Supp. 1, pp. 912-918, Mar. 2004.
Jun et al., Defining Human Embryo Phenotypes by Cohort-Specific Prognostic Factors, PLoS ONE 3(7):e2562, pp. 1-7 (2008).
Li et al., Analysis of Gene Expression in Single Human Oocytes and Preimplantation Embryos, Biochem. and Biophys. Res. Comm. 340(1):48-53 (2006).
Passmore et al., Assessing Decision Tree Models for Clinical In-Vitro Fertilization Data, Technical Report TR03-296, Department of Computer Science and Statistics, University of Rhode Island, Mar. 2004.
Minaretzis et al., Multivariate Analysis of Factors Predictive of Successful Live Births in In Vitro Fertilization (IVF) Suggests Strategies to Improve IVF Outcome, Journal of Assisted Reproduction and Genetics 15(6):365-371 (1998).

* cited by examiner

METHOD OF ASSESSING RISK OF MULTIPLE BIRTHS IN INFERTILITY TREATMENTS

CROSS REFERENCE TO RELATED APPLICATIONS

The present invention claims the benefit of U.S. Provisional Patent Application No. 61/363,650, filed on Jul. 13, 2010, which is incorporated by reference in its entirety herein.

TECHNICAL FIELD

The present invention relates generally to infertility treatments. More specifically, the present invention relates to method of assessing the risk of multiple births in a female human being undergoing infertility treatments.

BACKGROUND OF THE INVENTION

Among treatments for clinical infertility, assisted reproductive technologies (ART) have the highest live birth rate per treatment. Voorhis, *The New England Journal of Medicine* 356:379-386 (2007). ART has contributed to the conception of 1% of live births in the United States per year and more than 1 million babies worldwide since its inception. Bonduelle et al., *Human Reproduction (Oxford, England)* 20:413-419 (2005); Sunderam et al., *MMWR Surveill Summ* 58:1-25 (2009). There are, however, many medical, socio-economical, and ethical challenges associated with the implementation of ART that remain unresolved. For example, the decision of couples to pursue ART or to repeat ART treatment after a failed attempt is often a difficult decision due to the physical, emotional, and financial costs of treatment. Further, ART procedures provide no certainty regarding the outcome of a live birth event, a multiple birth event, or the associated maternal/fetal/neonatal complications associated with the live birth or multiple birth event.

With regard to multiple gestations, in the United States in 2006, ART contributed disproportionately to 18% of multiple gestations with 17% of the gestations being twins and 38% of the gestations being triplets or higher-order multiples; consequently 49% of ART infants were born from multiple gestations, compared to 3% in the general U.S. population. Sunderam et al., supra. Further, in 2006 in the U.S., 41% of ART infants were born preterm compared to the national preterm rate of 13%; therefore, ART contributed to 4% of all preterm births in the U.S. Sunderam et al., supra; Osterman et al., *National Vital Stat Rep* 57:1-104 (2009). Many preterm births in ART may be directly attributable to the high incidence of multiple gestations in ART. To illustrate, in 2006, 65% of ART twins and 13% of ART singletons were born preterm, compared to 11% in the general U.S. population. Similarly, 57% of ART twins, and 9% of ART singletons were born with low birth weight, compared to 6% in the general U.S. population. Sunderam et al. supra. While these national statistics potentially underestimate the differences since the general population might have comprised births conceived by ART and non-ART ovarian stimulation, the national statistics indicate that the ART population is at high risk for preterm birth and multiple gestations.

Many studies have reported increased risks of adverse obstetrical and neonatal outcomes in twin births resulting from ART. An exemplary study based on ART births retrieved from the Danish IVF/ICSI (in vitro fertilization/intracytoplasmic sperm injection) registry and its National Medical Birth Registry between 1995-2000 reported neonatal outcomes for 8602 births of which 40% were twins and 60% were singletons Pinborg et al., *Acta Obstetricia et Gynecologica Scandinavica* 83:1071-1078 (2004). Compared to ART singletons, ART twins had a 10-fold increased risk of preterm delivery prior to 37 gestational weeks and 7.4-fold increased risk of preterm delivery prior to 32 gestational weeks. In the U.K., ART twins had an 11-fold increased risk of low birth weight (<2500 g) and a 5-fold increased risk of very low birth weight (<1500 g). Sutcliffe et al., *Lancet* 370: 351-359 (2007). In addition, the incidence of stillbirths, cesarean section, and NICU admission were also increased for ART gestations. Similar findings have been reported by many ART centers. Id.

With regard to multiple birth events, presently, there are no validated prediction tools to assess the risks of multiple births in cases that have two or more embryos transferred. Efforts to minimize the risks of multiple gestations are challenged by the current lack of an optimal method for selecting patients for elective single embryo transfer (eSET), which is the procedure by which a single embryo is transferred to the uterus of an abstaining patient to completely eliminate the risk of having dizygotic twins, which is the predominant cause of multiple gestations, and hence preterm birth attributed to multiple gestations in ART. While eSET has been reported to decrease multiple gestation rates without compromising live birth rates by some, others have found that the implementation of eSET compromised per cycle or cumulative live birth rates and failed to reduce multiple gestation rates. Kalu et al., *BJOG* 115:1143-1150 (2008); Khalaf et al., *BJOG* 115:385-390 (2008); Styer et al., *Fertility and Sterility* 89:1702-1708 (2008).

Fertility physicians typically discuss the risk of multiple births with their patients prior to starting IVF or other fertility treatments, and then again just prior to embryo transfer (ET), which is the act of transferring embryos back to the womb. The discussion between the physician and the patient regarding the number of embryos to transfer is typically based on a discussion of the probabilities of multiple births and pregnancies as a function of the age of the female, the number of embryos transferred, and the embryo quality. When deciding whether to pursue multiple embryos or eSET, the physician typically adheres to the guidelines set forth by the American Society for Reproductive Medicine (ASRM). The ASRM has established guidelines for eSET patient selection that are largely based on the women's age and the total number of embryos. *Fertility and Sterility* 90:S163-164 (2008). Perhaps realizing the limitations of those guidelines, ASRM also recommends that each ART center use its own data to guide the number of embryos for transfer.

Following the guidelines established by the ASRM or Center for Disease Control (CDC), physicians and their patients are currently attempting to decrease the incidence of multiple births resulting from IVF by transferring fewer embryos, if not a single embryo. There is a general perception, however, that eSET decreases the probability of live births, but it is not known if there are specific subsets of patients who are at higher risks for multiple births. For example, it is possible that certain patients may be at very low risk for multiple births, but their probability of having a live birth may be significantly compromised if they were to pursue eSET instead of having two embryos transferred. In contrast, other patients may be at relatively high risk for multiple births, such that pursuing eSET may dramatically decrease their families' health risks. Presently, there is no way to determine if a particular female patient would benefit more from eSET than another patient.

The foregoing discussion demonstrates that multiple births are a significant health and socioeconomic problem for patients who are undergoing infertility treatment and that the current state of the art does not provide an effective way to be able to avoid multiple births and/or assure the success of eSET.

SUMMARY OF THE INVENTION

The present invention overcomes the shortcomings in the art by providing a method comprising analyzing data to predict a multiple birth event in a female human patient undergoing an infertility treatment, wherein the data is selected from the group consisting of the patient's age, the patient's ethnicity, the patient's medical and reproductive history, the patient's male partner's age, the patient's male partner's ethnicity, the patient's male partner's medical and reproductive history, the patient's response to hormonal control agents, number of oocytes obtained from the patient, number of embryos obtained from the patient, oocyte quality, egg quality, sperm quality, fertilization quality, embryo quality, embryo developmental parameters, embryology laboratory protocols, infertility treatment protocols, and combinations thereof.

In one embodiment of the invention, the patient's reproductive history may be selected from the group consisting of the patient's history of pregnancy, the patient's history of infertility, clinical diagnoses pertaining to the patient's infertility, laboratory tests, diagnostic or prognostic tests, and combinations thereof. The patient's male partner's reproductive history will typically comprise sperm analysis.

In another embodiment of the invention, the hormonal control agents are selected from the group consisting of sex and pregnancy hormones, gonadotropin releasing hormone agonists, gonadotropin releasing hormone antagonists, and gonadotropins. The sex and pregnancy hormones may be selected from the group consisting of estradiol, progesterone, and combinations thereof. The hormonal manipulation may comprise treatments that control the serum levels of the sex steroids and/or modulate the amount of sex steroids exposed to reproductive tissues.

In a further embodiment of the invention, the embryo developmental parameters are selected from the group consisting of morphology, cell number, developmental stage, developmental grade, molecular markers of development, and combinations thereof.

In another embodiment of the invention, the infertility treatment is selected from the group consisting of in vitro fertilization (IVF), intracytoplasmic sperm injection (ICSI), and combinations thereof.

In a further embodiment of the invention, the data may be obtained from a single clinic or from multiple clinics.

In another embodiment of the invention, a prediction of the multiple birth event triggers, precedes, or qualifies an embryo viability testing event.

In a further embodiment of the invention, the multiple birth prediction data analysis is performed by techniques selected from the group consisting of logistic regression, regression tree analysis, boosted tree analysis, and machine learning.

In another embodiment of the invention, the data may be entered into a software application that hosts at least one algorithm, wherein the least one algorithm may be selected from the group consisting of logistic regression, regression tree analysis, boosted tree analysis, machine learning. The software application may be run in real time or in batches.

In a further embodiment of the invention, the software application is integrated into a platform selected from the group consisting of a desktop computer, a laptop computer, a network, a web-based software-as-a-service application, a cloud server, a co-located server, a local server, a storage medium, a mobile device, a smart phone application, a hand-held device used in clinical settings, an electronic medical record, and a medical device. The medical device may be selected from the group consisting of an ultrasound machine, a microscope, quality control equipment, and diagnostic equipment.

In another embodiment of the invention, the data entered into the algorithm is data relating to one or more embryos of the female human patient, which may be selected from the group consisting of information obtained from culture media of one or more embryos, viability information obtained from non-invasive digital imaging of one or more embryos, information obtained from a biopsied embryo cell or cell fragment, gene expression analysis of one or more embryos, genomics analysis of one or more embryos, methylation site analysis of one or more embryos, proteomics analysis of one or more embryos, and combinations thereof. Cell fragments may be selected from the group consisting of a polar body, a blastomere, a degraded cell, an embryo with poor grade, and a trophoectoderm cell.

In a further embodiment of the invention, the information obtained from the culture media is selected from the group consisting of metabolites, secreted proteins, secreted peptides, lipids, carbohydrates, oxygen radicals, gas composition, cell-free DNA, cell-free RNA in the culture media, and combinations thereof.

In another embodiment of the invention, the viability information obtained from the non-invasive digital imaging of the one or more embryo is selected from the group consisting of cell divisional rate, morphologic measurements of sub-cellular structures, morphologic measurements of embryo cells relative to one another, position of embryo cells relative to one another, direction of cell division relative to position of dividing cells, direction of embryo cell division relative to cell population position, density of sub-cellular structures, spatial distribution of sub-cellular structures within a cell, spatial distribution of sub-cellular structures relative to cell population, and combinations thereof.

In a further embodiment of the invention, the genomics analysis is selected from the group consisting of chromosomal analysis whole genome sequencing, partial genome sequencing, transcriptome analysis, copy number variation analysis, and single nucleotide polymorphism (SNP) analyses. Genomics analysis may be carried out with an assay selected from the group consisting of fluorescent in situ hybridization (FISH), comparative genome hybridization (CGH), polymerase chain reaction (PCR), semi-quantitative real-time PCR, multiplex PCR, oligonucleotide or nucleotide arrays, antibody arrays, and chromatin immunoprecipitation.

In another embodiment of the invention, the methylation site analysis is selected from the group consisting of global DNA methylation, gene-specific DNA methylation, and combinations thereof.

In a further embodiment of the invention, an analysis obtained from the multiple birth prediction is applied to a diagnostic or prognostic platform or device to predict embryo viability in the female human patient. The diagnostic or prognostic platform or device typically measures one or more physiological, genetic, or developmental characteristics of the embryos, which may be selected from the group consisting of metabolite analysis of the embryos in culture medium, genetic defects of the embryos, genetic variants of the embryos, chromosomal defects of the embryos, chromosomal structural variants of the embryos, transciptomic profile of the embryos, rate of embryo cell division, morphological parameters, developmental measures, and combinations thereof. Morphological parameters may be determined by microscopic imaging, videoscopic imaging, or combinations thereof.

Additional aspects and embodiments of the invention will be provided, without limitation, in the detailed description of the invention that is set forth below.

DETAILED DESCRIPTION OF THE INVENTION

Set forth below is a description of what are currently believed to be preferred embodiments of the claimed invention. Any alternates or modifications in function, purpose, or structure are intended to be covered by the claims of this application. As used in this specification and the appended claims, the singular forms "a," "an," and "the" include plural referents unless the context clearly dictates otherwise. The terms "comprises" and/or "comprising," as used in this specification and the appended claims, specify the presence of stated features, integers, steps, operations, elements, and/or components, but do not preclude the presence or addition of one or more other features, integers, steps, operations, elements, components, and/or groups thereof.

Within the context of the present invention, the term "patient" refers to a female human being undergoing infertility treatments.

The term "infertility treatments" refers to the use of oral or injectable medications to induce ovulation or to stimulate the ovaries to produce more than one mature egg (i.e., an egg that can be fertilized to result in an embryo). Within the context of the present invention, the term "infertility treatments" is meant to include natural conception that is aided by artificial insemination, IVF, and/or ICSI. The term "infertility treatments" is also meant to include the enhancement of natural, induced, or stimulated cycle by cycle monitoring, with or without medical intervention or medications; in this respect, the aim of the infertility treatments is to improve the viability of the embryos that are conceived in vivo (e.g., after artificial insemination or by natural cycle) or that are transferred to the uterus, after IVF, ICSI, embryo cryopreservation-thawing, or any other assisted reproductive technology.

The terms "assisted reproductive technologies," "assisted reproductive technology," and "ART" refer to treatments that involve in vitro (outside of the body) manipulation of gametes (eggs and sperm at any stage of maturity). Predominant types of ART include without limitation: (i) in vitro fertilization (IVF), which entails surgical retrieval of eggs from the body and fertilization in vitro followed by in vitro culture of the embryos and transfer of the embryos back into the body; (ii) intracytoplasmic sperm injection (ICSI), which is the same as IVF except that sperm is singly microinjected into each egg to bypass the natural process of fertilization; (iii) gamete intrafallopian transfer (GIFT), wherein retrieved eggs and processed sperm are placed into fallopian tubes in a surgical procedure (laparoscopy) and subsequent fertilization and conception occurs within the body; (iv) use of cryopreserved embryos from IVF or ICSI procedures; (v) use of eggs from a female donor; (vi) use of sperm from a male donor; (vii) placement of embryos into the womb of a surrogate mother; and (viii) use of cryopreserved eggs (not embryos) or sperm.

The term "multiple birth event" refers to the birth of two or more fetuses or babies from a single pregnancy that has reached at least 20 weeks of gestation, regardless of the viability of the individual fetuses at birth or the baby after birth. By contrast, the term "multiple gestation event" refers to the concurrent viability of two or more embryos that have implanted in the womb and develop to any stage of pregnancy at which one or more embryos may become non-viable or continue to be viable. Within the context of the present invention, a multiple birth event is meant to encompass and include a multiple gestation event. A multiple birth event will typically occur as a direct result of an infertility treatment (which by definition may include one or more assisted reproductive technologies). It is to be understood that the term "multiple birth event" differs from the terms "live birth," "live birth rate," or "live birth event," all of which refer to a successful treatment that results in the birth of a live baby. For example, a discussion about "live birth" in the context of infertility treatment is typically focused on whether a treatment is successful, and not whether it produces multiple births or multiple gestations and their associated complications.

The term "MBP" or "MBP prognostic tool" are used interchangeably to refer to the multiple birth prediction test of the present invention.

The term "posterior log of odds ratio" or "PLORA" test uses Bayesian statistics, log likelihood, or other measures to calculate posterior probabilities. In addition, other measures of posterior probabilities such as log likelihood, relative log likelihood, and/or improvement in log likelihood may also be used.

The term "area under the curve" or "AUC" measures discrimination based on the true and false positive rates at a series of arbitrarily defined thresholds. The term "receiver operator curve" or "ROC" measures how well a test balances the ability to predict an outcome when it would occur with the chance that a prediction would truly occur. In prognostics, AUC/ROC measures discrimination—the ability of a prediction model to discriminate patients who have poor prognosis versus those who have good prognosis. Within the context of the present invention, the AUC refers to the area under the curve of the ROC. In the best case scenario, when 100% of outcomes can be predicted (i.e., true positive rate is 100% and false positive rate is 0%), AUC=1. AUC=0.5 indicates that the prediction is no better than tossing a coin, while AUC<0.5 indicates that the prediction is worse than tossing a coin.

In IVF treatments, it is generally believed that the number of embryos transferred back into a patient largely determines the number of gestations or neonates. The multiple birth prediction (MBP) prognostic tool of the present invention allows for a determination of whether or not a certain number of embryo(s) will implant resulting in a viable clinical pregnancy that will ultimately lead to a live birth event. For example, the MBP prognostic tool may be used on the day of embryo transfer to inform patients of their personalized risk of multiple births in IVF treatments where two or more embryos are transferred to the womb. To run the MBP prognostic tool, the use of patient-specific data allows for the personalized assessment of a multiple gestation event, a multiple birth event, and/or the viability of a certain number of embryo(s).

An advantage of the MBP prognostic tool of the present invention is that it allows for the identification of patients who are at high risk for multiple gestations, and/or for whom eSET may be highly recommended. By providing the patient-specific risk for a multiple birth event, the patient may be more likely to assess eSET. Patients who use eSET will have decreased chance to experience the associated neonatal complications that accompany a multiple birth event, such as for example, prematurity, low birth weight, preeclampsia, and abruption. While single embryo transfers can result in a multiple birth event (typically monozygotic twinning, which is also associated with obstetrical and neonatal complications), the prevalence of monozygotic twinning resulting from the transfer of a single embryo is significantly lower than the prevalence of a multiple birth event resulting from the transfer of multiple embryos.

By using the MBP prognostic tool in the manner described herein, the patient and the physician may be able to enhance identification of embryos that are most viable, so that the transfer of only one or two embryos would not compromise the probability of live birth event from a single IVF treatment. Alternatively or additionally, the MBP prognostic tool of the present invention may be used to identify patients who are at relatively high risk of having a multiple birth event if more than one embryo was transferred to the womb (or if more than one egg was to ovulate in a treatment using natural conception or artificial insemination). Such patients would benefit the most from having embryo viability tests performed for the purpose of selecting the most viable embryo(s) for transfer.

Data that may be used to run the MBP prognostic tool of the present invention includes without limitation, the patient's age, the patient's ethnicity, the patient's medical and reproductive history, the patient's male partner's age, the patient's male partner's ethnicity, the patient's male partner's medical and reproductive history, the patient's response to hormonal control agents, number of oocytes obtained from the patient, number of embryos obtained from the patient, oocyte quality, egg quality, sperm quality, fertilization quality, embryo quality, embryo developmental parameters, embryology laboratory protocols, infertility treatment protocols, and combinations thereof.

Hormonal manipulation typically will include treatments that control or modulate the amount of sex steroids exposed to reproductive tissues. The patient's response to the hormonal manipulation may include without limitation, endometrial thickness (as measured by ultrasound) and/or serum peak estradiol levels. Hormonal control agents contemplated under the present invention include without limitation, sex and pregnancy hormones, such as estradiol and progesterone; gonadotropin releasing hormone agonists, gonadotropin releasing hormone antagonists, and gonadotropins. Embryo developmental parameters contemplated under the present invention include without limitation, morphology, cell number, developmental stage, developmental grade, molecular markers of development, and combinations thereof.

Data can be collected directly from the patients, paper charts in the clinics, electronic medical records, electronic personal health records, or a combination of any of the foregoing. The data used to run the MBP prognostic tool will typically be prepared by the healthcare provider, patient or consumer, or by both the healthcare provider and patient jointly. In a preferred embodiment, the report will have user-friendly language providing a description of the test, its interpretation and limitations, and graphic presentation to facilitate communications between the physician and the patients.

In one embodiment of the invention, the multiple birth prediction data analysis is performed by techniques selected from the group consisting of logistic regression, regression tree analysis, boosted tree analysis, and machine learning. In another embodiment of the invention, the multiple birth prediction data is entered into a software application that hosts at least one algorithm that includes without limitation, logistic regression, regression tree analysis, boosted tree analysis, machine learning. Data entered into the algorithm may be data relating to one or more embryos of the female human patient, including without limitation, information obtained from culture media of one or more live embryos, viability information obtained from non-invasive digital imaging of one or more embryos, information obtained from a biopsied embryo cell or cell fragment, gene expression analysis of one or more embryos, genomics analysis of one or more embryos, methylation site analysis of one or more embryos, proteomics analysis of one or more embryos, and combinations thereof. Examples of cell fragments include without limitation, polar bodies, blastomeres, degraded cells, embryos with poor grade, and trophoectoderm cells.

Examples of information obtained from the embryo culture media includes without limitation, information relating to metabolites, such as ammonium and glucose; secreted proteins; secreted peptides; lipids; carbohydrates; oxygen radicals; gas composition; cell-free DNA; and cell-free RNA. The usefulness of the information and its quantitative (or semi-quantitative) levels may differ according to the patient's risk of a multiple birth event). Examples of gene expression include without limitation, Oct4, Sall4, and Nanog expression levels. Examples of genomics analyses include without limitation, chromosomal analyses whole genome sequencing, partial genome sequencing, transcriptome analyses, and copy number variation analyses, single nucleotide polymorphism (SNP) analyses. Examples of assays to carry out the foregoing genomic analyses includes without limitation, fluorescent in situ hybridization (FISH), comparative genome hybridization (CGH), polymerase chain reaction (PCR), semi-quantitative real-time PCR, multiplex PCR, oligonucleotide or nucleotide arrays (i.e., "gene chips"), antibody arrays, and chromatin immunoprecipitation. It is to be understood that the genomic analyses and assays set forth herein may be applied to both genomic DNA and genomic RNA. Examples of methylation site analysis include without limitation, global DNA methylation and gene-specific DNA methylation.

An example of a non-invasive analysis of an embryo is digital imaging of the embryo, which may measure one or more of the following characteristics of the embryo: embryo cell divisional rate, morphologic measurements of sub-cellular structures, morphologic measurements of embryo cells relative to one another, position of embryo cells relative to one another, direction of cell division relative to position of dividing cells, direction of embryo cell division relative to cell population position, density of sub-cellular structures, spatial distribution of sub-cellular structures within a cell, and spatial distribution of sub-cellular structures relative to cell population In another embodiment of the invention, the data obtained to run the MBP prognostic tool may be entered into a software application hosting the MBP algorithm, which can be ordered to run in real-time or in batches. In contrast to other fertility clinical decision support systems (CDSSs), with embryo transfer (ET), there is a very narrow window between the time when all the clinical data is available to decision-making and the time that the ET must occur; accordingly, the software application must be readily available to the patient and their physician. In one embodiment of the invention, the software application is integrated into a platform that may include without limitation, a desktop computer, a laptop computer, a network, a web-based software-as-a-service application, a cloud server, a co-located server, a storage medium (e.g., CD, memory stick, or thumb drive), a mobile device, a smart phone application, a hand-held device used in a clinic setting, an electronic medical record, or a medical device. Examples of medical devices that may be used to host MBP prognostic tool of the present invention include without limitation, an ultrasound machine; a device used by clinical embryology laboratories to support in vitro culture, such as a microscope; quality control equipment; and diagnostics equipment, such as a device that is used to analyze or report embryo viability.

Using the MBP prognostic tool of the present invention, physicians can counsel IVF patients regarding the option of eSET and the risks of a multiple birth event based on a predictive model that is developed and validated by analyzing diverse cases and patients, to provide an assessment of the personalized probability of a multiple birth event. By using a personalized prediction of multiple births probabilities, the patient and physician can make an informed decision regarding whether or not to pursue embryo selection based upon embryo viability testing. For example, if the risk of a multiple birth event is very high, embryo viability testing may be beneficial to the patient in order to determine the number of viable embryos that should be transferred to the patient in order to avoid a multiple birth event. In contrast, if the risk of a multiple birth event is low, then the cost-benefit ratio of having embryo viability testing may be limited, since the patient is relatively less likely to experience a multiple birth event regardless of the viability or number of embryos transferred to the patient. Because embryo viability testing is typically an expensive process, having an evidence-based manner for recommending embryo viability testing to patients is an important part of the counseling and decision-making steps.

The MBP prognostic tool of the present invention can do any of the following: (i) identify IVF patients who are at high risks for multiple births if two or more embryos are transferred; (ii) identify IVF patients whose multiple birth risks are not altered by transferring two embryos versus eSET; (iii) identify IVF patients whose likelihood of live birth outcomes would be severely compromised by eSET; (iv) identify IVF patients whose likelihood of live birth outcomes would not be affected by eSET; (v) identify IVF patients who belong to any two of the groups listed above; and (vi) support highly personalized counseling prior to starting IVF and just prior to ET.

In one embodiment of the present invention, the MBP prognostic tool of the present invention is applied to a diagnostic or prognostic platform or device to predict embryo viability in the female human patient. Diagnostic or prognostic platforms that may be used with the MBP prognostic tool of the present invention will typically measure one or more parameters including, but not limited to, physiological, genetic, and developmental characteristics of the embryos. Physiological, genetic, and/or developmental characteristics of the embryos will typically include parameters such as, metabolite analysis of the embryos in culture medium, genetic defects of the embryos, genetic variants of the embryos, chromosomal defects of the embryos, chromosomal structural variants of the embryos, transciptomic profile of the embryos, rate of embryo cell division, morphological parameters, and developmental measures. Morphological parameters are typically studied using microscopic imaging and/or videoscopic imaging.

The predictors of multiple birth risk for a specific patient in a specific infertility treatment, and the relative importance of the predictors may be different among some clinics. Inter-clinic differences include without limitations, differences in treatment protocols; embryology laboratory protocols; procedures for culturing oocytes and embryos (i.e., IVF versus ICSI); embryo selection criteria transfer or cryopreservation; physical environment; equipment calibration; and embryo transfer methods. Inter-clinic differences in MBP predictors and their relative importance indicate that clinical factors that are prognostic in one clinic may not have the same prognostic value in a different clinic.

In one embodiment of the invention, the MBP prognostic tool is developed and validated for a single clinic. As a clinic-specific prognostic tool, the MBP is used for only that specific clinic. In another embodiment of the invention, the MBP prognostic tool is validated and applied to multiple clinics. As a multi-clinic prognostic tool, the MBP is preferably used with clinics that share commonalities among protocols such that the same clinical variables are prognostic for each clinic and the relative importance of those prognostic factors are sufficiently similar for each clinic that it makes sense for them to use the same MBP. Within the context of the present invention, the data used to prepare the single or multiple clinic prognostic tools may be the raw data itself or, if more appropriate, the mathematical relationships among the data and/or the influence of the data on multiple birth probabilities.

Since the MBP prognostic tool of the present invention may be dependent upon a clinic's protocols, clinical practice style, and criteria for selecting patients for eSET or embryo viability testing, all of which may influence the relative prognostic value of clinical variables, the MBP may change as a result of changes in a clinic's protocols or its patient population. In this regard, the MBP prognostic tool may need to be changed periodically in order to take into consideration recent changes to a clinic's protocols, practice style, and patient and eSET selection criteria. In a preferred embodiment of the invention, the MBP prognostic tool is subject to annual review.

It is to be understood that while the invention has been described in conjunction with the embodiments set forth above, the foregoing description as well as the examples that follow are intended to illustrate and not limit the scope of the invention. Further, it is to be understood that the embodiments and examples set forth herein are not exhaustive and that modifications and variations of the invention will be apparent to those of ordinary skill in the art without departing from the scope and spirit of the invention.

All patents and publications mentioned herein are incorporated by reference in their entireties.

EXPERIMENTAL

The following examples are set forth to provide those of ordinary skill in the art with a complete disclosure of how to make and use the aspects and embodiments of the invention as set forth herein. Unless indicated otherwise, parts are parts by weight, temperature is degrees centigrade, and pressure is at or near atmospheric. All components were obtained commercially unless otherwise indicated.

Example 1

Generation of MBP and Age-Control Models

Methodology to Prepare the MBP and Age-Control Models

Regression tree and boosted tree methods are used to identify significant, non-redundant prognostic factors that influence the risk of multiple births in the ART population. The prognostic factors identified by the regression tree and boosted tree methods are used to generate the MBP and age-control models described herein.

MBP models are established from a set of 250 to 500 IVF treatments with live birth outcomes resulting from a transfer of at least two embryos into female human patients.

For external validation, MBP models are established from a set of 100-250 IVF treatments with live birth outcomes resulting from a transfer of at least two embryos into female human patients.

An MBP model, i.e., MBP-1 is generated according to the foregoing procedures. The control model uses age as the only prognostic factor to predict the probability of having multiple births. The rationale for using the patient's chronological age is that according to the ASRM guidelines, age is the primary factor used to assess the risk of multiple births and to select patients for single embryo transfer (eSET).

MBP-1 is compared to the age-control model in the following statistical comparisons. The results will demonstrate that the age of the patient (i.e., the primary factor proposed by the sASRM and CDC guidelines for eSET selection) is not a significant predictor of the risk of multiple births in IVF.

Example 2

Statistical Comparison of MBP and Age-Control Models

The PLORA Test

The PLORA test is used to calculate posterior probabilities of predicting multiple births by MBP-1 versus age-control as follows:

PLORA for MBP-1=3.0 (log scale) and 20 (linear scale).

Statistical conclusion: MBP-1 provides an improved fit for multiple birth outcomes at a ratio of 20:1 compared to the age-control model.

Interpretation: MBP-1 provides an improved ability to predict multiple birth outcomes in IVF by 20 folds compared to the age-control model.

PLORA for age-control is set at 0 (log scale) and 1 (linear scale).

Example 3

Statistical Comparison of MBP and Age-Control Models

The AUC/ROC Test

The AUC/ROC test is used to predict improved ability to discriminate patients who are at different risks of having multiple births in fresh IVF-ET treatments that use at least two embryos, compared to using age alone as follow:

AUC of MBP-1=0.70; AUC of age-control=0.6.

MBP-1 provides 16.7% improved ability to discriminate patients who are at different risks of having multiple births in fresh IVF-ET treatments that use at least two embryos, compared to using age alone.

Example 4

Statistical Comparison of MBP and Age-Control Models

Dynamic Range of Prediction and Reclassification

In addition to statistical analyses, the applicability of a prognostic tool also depends on the dynamic range of predicted probabilities and the percentage of the patient population that would be "reclassified" as having a significantly different, yet more accurate, probability of having multiple births compared to the age-control model.

Instead of being told one of three probabilities of multiple births ranging from ~20% to ~40% based on the patient's age, a patient would be informed by the MBP-1 model to have a specific probability of multiple births between the dynamic range of ~10% to over 60%. Using the MBP-1 model of Example 1, ~58% of patients under 42 years of age would be reclassified to have a different probability of multiple births than predicted by age alone.

Example 5

Analysis of Concurrent Viability of Embryos

A female human patient undergoing infertility treatment has 7 embryos and must decide to transfer one or more embryos. She undergoes embryo viability testing on one or more diagnostic platforms that use biologic analytics, such an embryo biopsy, to perform single cell gene expression analysis, e.g., one cell biopsied from each embryo. Receipt of the embryo biopsy report provides the patient and her health care provider with the probability of pregnancy or a live birth if the patient were to have one embryo transferred.

By applying the MBP method of the present invention, the patient also receives a report of the probability of a multiple birth event if any two of the embryos are transferred, thus informing the patient and her health care provider which two embryos may provide optimal live birth probabilities while minimizing the probability of a multiple birth event.

I claim:

1. A method comprising:
(a) selecting data specific to a female human patient at pre-in vitro fertilization (pre-IVF) or at a pre-embryo transfer (pre-ET) step of an IVF treatment, wherein the data is selected from the group consisting of the patient's age, the patient's ethnicity, the patient's medical and reproductive history, the patient's male partner's age, the patient's male partner's ethnicity, the patient's male partner's medical and reproductive history, the patient's response to hormonal control agents, number of oocytes obtained from the patient, number of embryos obtained from the patient, oocyte quality, egg quality, sperm quality, fertilization quality, embryo quality, embryo developmental parameters, embryology laboratory protocols, infertility treatment protocols, and combinations thereof;
(b) entering the data of step (a) into a software application that analyzes data to predict the likelihood that the pre-IVF or pre-ET-female human patient will experience a multiple birth event, wherein the software application hosts at least one algorithm and is run in real time or in batches and the prediction of the multiple birth event triggers, precedes, or qualifies an embryo viability testing event; and
(c) conducting an embryo viability test to select viable embryos for transfer to the female human patient, wherein the selection of the viable embryos transferred to the female human patient is based upon the multiple birth prediction of step (b).

2. The method of claim 1, wherein the patient's reproductive history is selected from the group consisting of the patient's history of pregnancy, the patient's history of infertility, clinical diagnoses pertaining to the patient's infertility, laboratory tests, diagnostic or prognostic tests, and combinations thereof.

3. The method of claim 1, wherein the patient's male partner's reproductive history comprises sperm analysis.

4. The method of claim 1, wherein the hormonal control agents are selected from the group consisting of sex and pregnancy hormones, gonadotropin releasing hormone agonists, gonadotropin releasing hormone antagonists, and gonadotropins.

5. The method of claim 4, wherein the sex and pregnancy hormones are selected from the group consisting of estradiol, progesterone, and combinations thereof.

6. The method of claim 1, wherein the patient's response to hormonal control agents comprises treatments that control sex steroid serum levels.

7. The method of claim 1, wherein the patient's response to hormonal control agents comprises treatments that modulate sex steroid amounts that are exposed to reproductive tissues.

8. The method of claim 1, wherein the embryo developmental parameters are selected from the group consisting of morphology, cell number, developmental stage, developmental grade, molecular markers of development, and combinations thereof.

9. The method of claim 1, wherein the infertility treatment protocols are selected from the group consisting of in vitro fertilization (IVF), intracytoplasmic sperm injection (ICSI), and combinations thereof.

10. The method of claim 1, wherein the data is obtained from a single clinic.

11. The method of claim 1, wherein the data is obtained from multiple clinics.

12. The method of claim 1, wherein the at least one algorithm is selected from the group consisting of logistic regression, regression tree analysis, boosted tree analysis, machine learning.

13. The method of claim 12, wherein data entered into the software application is data relating to one or more embryos of the female human patient.

14. The method of claim 13, wherein data entered into the software application is selected from the group consisting of information obtained from culture media of one or more embryos, viability information obtained from non-invasive digital imaging of one or more embryos, information obtained from a biopsied embryo cell or cell fragment, gene expression analysis of one or more embryos, genomics analysis of one or more embryos, methylation site analysis of one or more embryos, proteomics analysis of one or more embryos, and combinations thereof.

15. The method of claim 14, wherein the information obtained from the culture media of one or more embryos is selected from the group consisting of metabolites, secreted proteins, secreted peptides, lipids, carbohydrates, oxygen radicals, gas composition, cell-free DNA, cell-free RNA in the culture media, and combinations thereof.

16. The method of claim 14, wherein the viability information obtained from the non-invasive digital imaging of the one or more embryo is selected from the group consisting of cell divisional rate, morphologic measurements of sub-cellular structures, morphologic measurements of embryo cells relative to one another, position of embryo cells relative to one another, direction of cell division relative to position of dividing cells, direction of embryo cell division relative to cell population position, density of sub-cellular structures, spatial distribution of sub-cellular structures within a cell, spatial distribution of sub-cellular structures relative to cell population, and combinations thereof.

17. The method of claim 14, wherein the cell fragment is selected from the group consisting of a polar body, a blastomere, a degraded cell, an embryo with poor grade, and a trophoectoderm cell.

18. The method of claim 14, wherein the genomics analysis is selected from the group consisting of chromosomal analysis whole genome sequencing, partial genome sequencing, transcriptome analysis, copy number variation analysis, and single nucleotide polymorphism (SNP) analyses.

19. The method of claim 18, wherein the genomics analysis is carried out with an assay selected from the group consisting of fluorescent in situ hybridization (FISH), comparative genome hybridization (CGH), polymerase chain reaction (PCR), semi-quantitative real-time PCR, multiplex PCR, oligonucleotide or nucleotide arrays, antibody arrays, and chromatin immunoprecipitation.

20. The method of claim 14, wherein the methylation site analysis is selected from the group consisting of global DNA methylation, gene-specific DNA methylation, and combinations thereof.

21. The method of claim 1, wherein the software application is integrated into a platform selected from the group consisting of a desktop computer, a laptop computer, a network, a web-based software-as-a-service application, a cloud server, a co-located server, a local server, a storage medium, a mobile device, a smart phone application, a hand-held device used in clinical settings, an electronic medical record, and a medical device.

22. The method of claim 21, wherein the medical device is selected from the group consisting of an ultrasound machine, a microscope, quality control equipment, and diagnostic equipment.

23. The method of claim 1, wherein embryos of the female human patient are tested for viability via a diagnostic or prognostic platform or device that measures one or more physiological, genetic, or developmental characteristics of the female human patient's embryos.

24. The method of claim 23, wherein the one or more physiological, genetic, or developmental characteristics of the female human patient's embryos is selected from the group consisting of metabolite analysis of the embryos in culture medium, genetic defects of the embryos, genetic variants of the embryos, chromosomal defects of the embryos, chromosomal structural variants of the embryos, transcriptomic profile of the embryos, rate of embryo cell division, morphological parameters, developmental measures, and combinations thereof.

25. The method of claim 24, wherein the morphological parameters are determined by microscopic imaging, videoscopic imaging, or combinations thereof.

* * * * *